(12) United States Patent
Picken, Jr. et al.

(10) Patent No.: US 9,610,374 B2
(45) Date of Patent: Apr. 4, 2017

(54) COMBINATION AIR FRESHENER, ODOR ABSORBER AND MOISTURE ABSORBER

(71) Applicants: Henry M. Picken, Jr., Panama City, FL (US); Jeffrey M. Picken, Marietta, GA (US)

(72) Inventors: Henry M. Picken, Jr., Panama City, FL (US); Jeffrey M. Picken, Marietta, GA (US)

(73) Assignee: Beaumont Products, Inc., Kennesaw, GA (US)

( * ) Notice: Subject to any disclaimer, the term of this patent is extended or adjusted under 35 U.S.C. 154(b) by 189 days.

(21) Appl. No.: 14/598,907

(22) Filed: Jan. 16, 2015

(65) Prior Publication Data

US 2015/0196678 A1    Jul. 16, 2015

Related U.S. Application Data

(60) Provisional application No. 61/928,201, filed on Jan. 16, 2014.

(51) Int. Cl.
*A62B 7/08* (2006.01)
*A61L 9/014* (2006.01)
*B01D 53/04* (2006.01)

(52) U.S. Cl.
CPC .......... *A61L 9/014* (2013.01); *B01D 53/0415* (2013.01); *B01D 2257/80* (2013.01); *B01D 2257/90* (2013.01)

(58) Field of Classification Search
CPC ............................. A61L 9/014; B01D 53/261
See application file for complete search history.

(56) References Cited

U.S. PATENT DOCUMENTS

| | | | |
|---|---|---|---|
| 2,555,047 A | 10/1948 | Logue | |
| 5,695,692 A * | 12/1997 | Kennedy | A61L 9/125 239/60 |
| D491,257 S | 6/2004 | Picken | |
| 9,227,164 B2 * | 1/2016 | Sherman | B01F 13/0049 |
| 2005/0031498 A1* | 2/2005 | Held | A61L 9/12 422/124 |
| 2009/0218413 A1* | 9/2009 | Withers | A61L 9/035 239/6 |
| 2014/0186224 A1* | 7/2014 | Derby Krans | A61L 9/014 422/120 |

\* cited by examiner

*Primary Examiner* — Kevin Joyner
(74) *Attorney, Agent, or Firm* — Thomas | Horstemeyer, LLP

(57) ABSTRACT

A multiple purpose container for an air freshener, odor absorber and moisture absorber in a single product includes a tub with a lid that has openings, a basket suspended in the tub that has a vertical partition for holding an air freshener on one side and a moisture absorber on the other side, the basket includes openings on one side of the vertical partition that holds the moisture absorber to allow liquid absorbed to drain from the basket to the space below the basket.

7 Claims, 5 Drawing Sheets

COMBINATION AIR FRESHENER, ODOR ABSORBER AND MOISTURE ABSORBER

PRIORITY CLAIM

Applicants claim priority to U.S. Provisional Patent Application 61/928,201 filed in the U.S. Patent and Trademark Office on Jan. 16, 2014.

SUMMARY OF THE INVENTION

This invention concerns a multiple purpose product that includes an air freshener, odor absorber and moisture absorber in a single package.

BACKGROUND

Usually, prior art air fresheners, odor absorbers and moisture absorbers are purchased individually and used separately. The products usually are purchased one at a time by the typical purchasers.

Since water absorbents generally collect moisture from the air and convert it into water, the collected water must be separately emptied and the retention of water is not compatible with contacting air fresheners and odor absorbers. Further, it has been found that the typical purchaser will purchase the three items at different times since the products are distinct and have different functions.

If the moisture absorber product is combined with the air freshener or odor absorber, there are potential problems of retaining and later emptying the collected water from the product. This makes the combination of the moisture absorber undesirable when combined with one of the other products.

It would be desirable to produce a combination product in which the functions of air freshening, odor absorbing, and moisture collection are compatible with one another and which includes a convenient arrangement for collecting and retaining liquid and later emptying the collected liquid from the container without disturbing the air freshener and/or odor absorber.

Thus, it is an object of this invention to provide a multiple purpose air freshener, odor absorber and moisture absorber in a single product that may be conveniently used by the purchaser, with a means for conveniently emptying water from the combination device without deterioration of the contents of the combination product.

DETAILED DESCRIPTION

Figure 1:
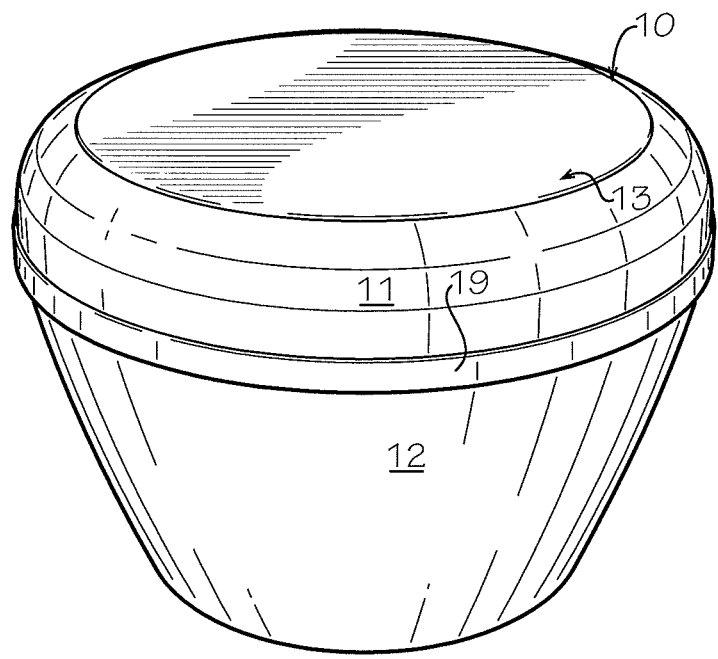
FIG. 1 is a perspective exterior view of the assembled air freshener, odor absorber and moisture absorber, hereinafter referred to as the "product."

Referring now in more detail to the drawings in which like numerals indicate like parts throughout the several views, FIG. 1 illustrates the product 10 that includes lid 11 and tub 12, with the lid mounted firmly to the upper rim of the tub. The rim of the tub and the opposed rim of the lid are complementary in shape so that the lid may be firmly fastened to the tub by urging the lid into a connection with the tub.

Figure 2:
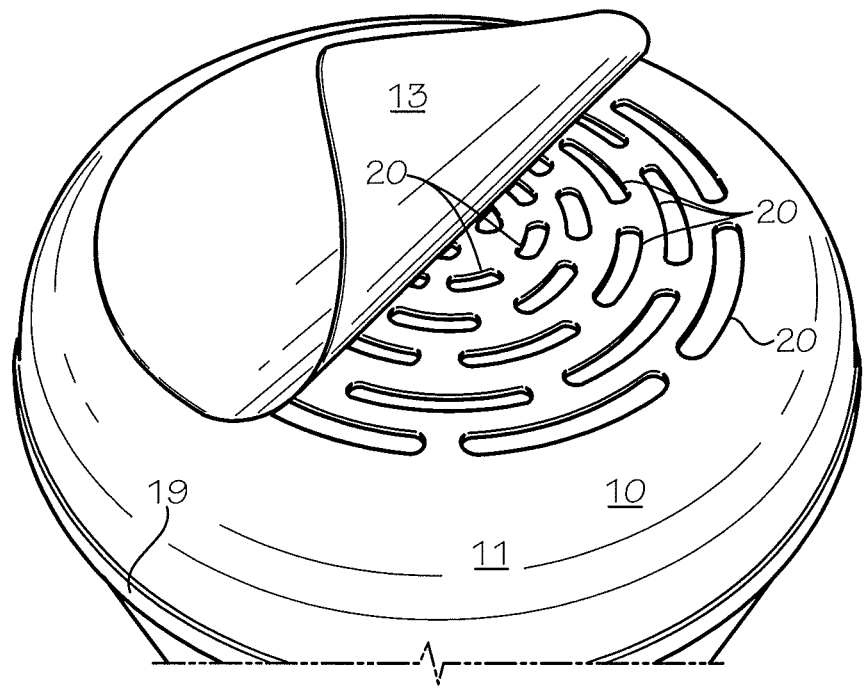
FIG. 2 is a perspective view of the exterior of the lid and the label of the product as they are applied to the tub, showing the label partially peeled away from the lid.

As shown in FIG. 2, a label 13 is adhesively mounted to the upper surface of the lid 11 so that the label may be peeled back away from the lid to expose the openings 20 in the lid. The label 13 may be partially removed or fully removed from the lid to control the rate of atmospheric contact with the solid air freshener and moisture absorber and odor absorber. Also, the label 13 may be partially removed in a configuration to expose more of one of the products than the other. The openings 20 in the lid 11 may be arranged in a lattice of oblong shapes arranged in concentric circles extending from the center of the lid out toward the sides of the lid. The lid is curved downwardly to form its lower rim 19.

Figure 3:
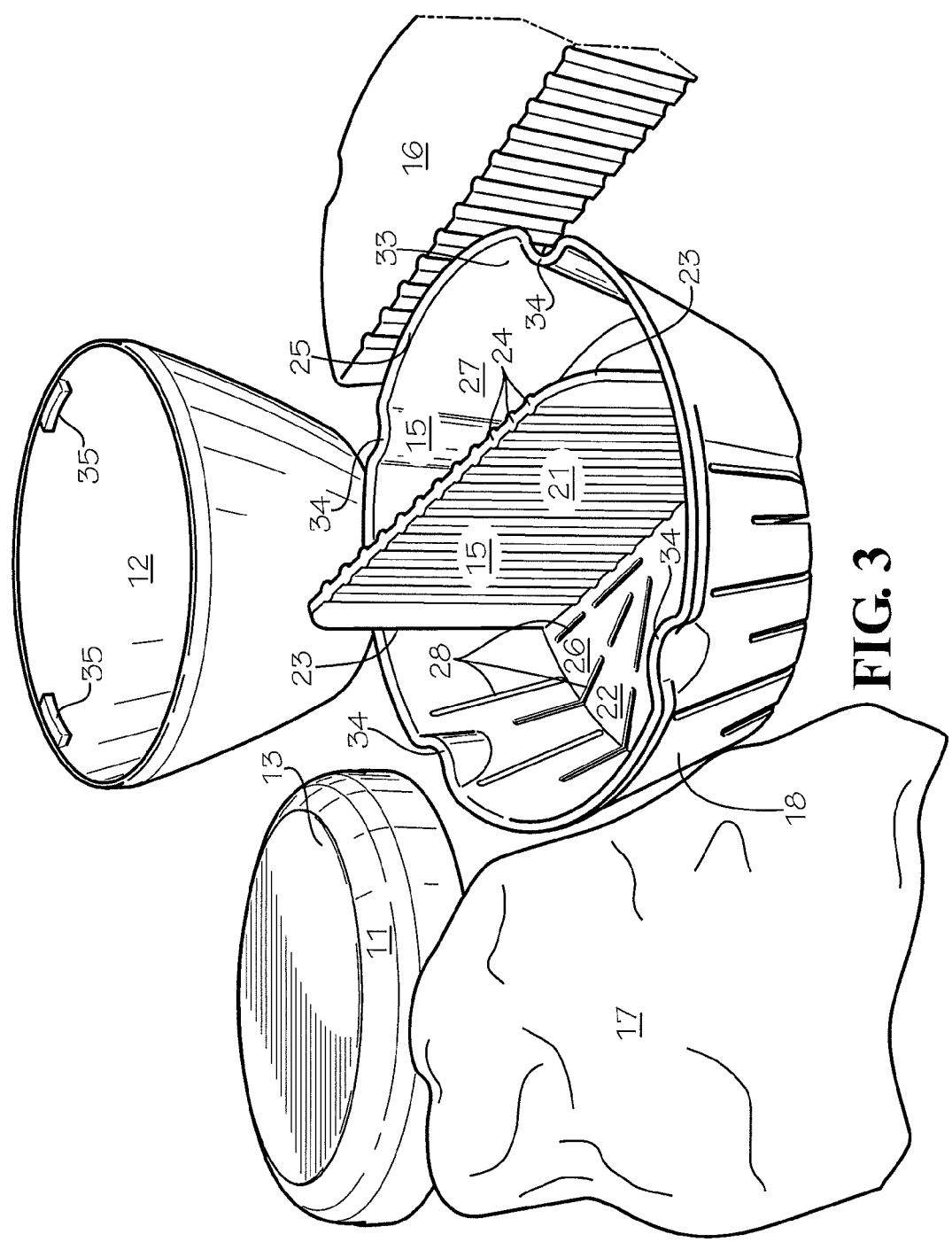
FIG. 3 is a perspective view of all the components of the product, disassembled from one another, including the tub, the basket, the solid air freshener and odor absorber and the granular moisture absorber contained in an impervious envelope, the lid and the label applied to the lid.

FIG. 3 shows the product disassembled. The solid air freshener and odor absorber 16 is formed first in a liquid condition and is poured into the impervious chamber 27 of the basket 15 to lose its temperature and solidify and take the shape of the basket.

Basket 15 includes an annular side wall 18, a vertical divider 21 that may be positioned diagonally in the basket and connected at its side edges to the annular side wall 18, extending from the bottom wall 22 of the basket in an upward direction toward the lid 11. The side edges 23 of the vertical divider may engage and be formed integrally with the upwardly extending annular side wall 18 of the basket 15, in a sealed relationship with the bottom wall and side wall. The vertical divider 21 may extend higher than the annular side wall 18 of the basket and preferably is formed with a plurality of ribs 24 that extend upwardly from the bottom wall 22 of the basket. The vertical divider 21 divides the interior of the basket 15 into separate chambers with the porous chamber 26 on one side of the vertical divider and an impervious chamber 27 on the other side of the vertical divider. Also, the annular side wall and the bottom wall of the basket on the porous side of the basket are formed with open slots 28 with the open slots extending radially from the center of the bottom wall 22 and upwardly through the adjacent portion of the side wall of the basket.

As shown in FIG. 3, the granular moisture absorber 17 is initially provided in an impervious, transparent bag in a quantity that will fit into the porous section of the basket. When the granular moisture absorber is poured from its bag into the porous side of the basket the open slots 28 are small enough so as to maintain the granules of the moisture absorber in the basket but large enough to allow moisture to drain from the moisture absorber downwardly from the basket into the bottom of the tub 12.

Figure 4:
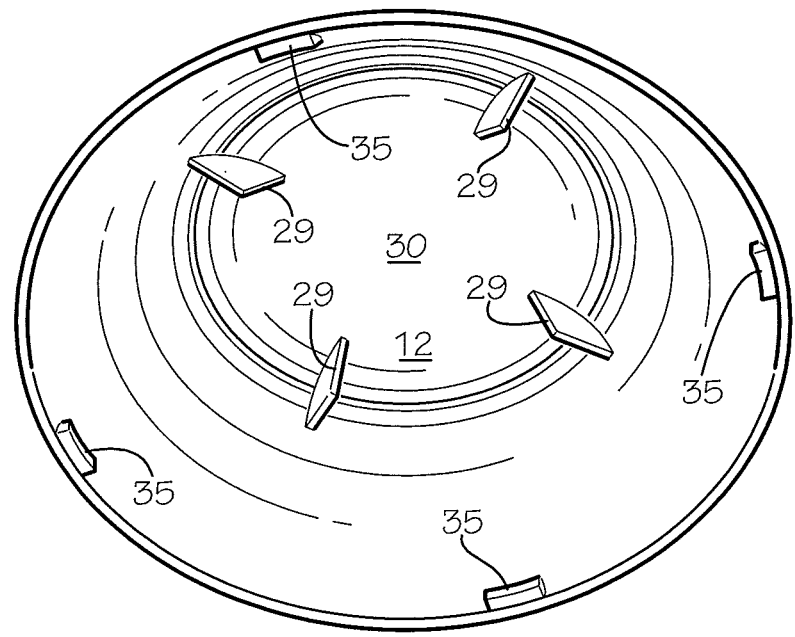
FIG. 4 is a view of the interior of the tub.
Figure 5:
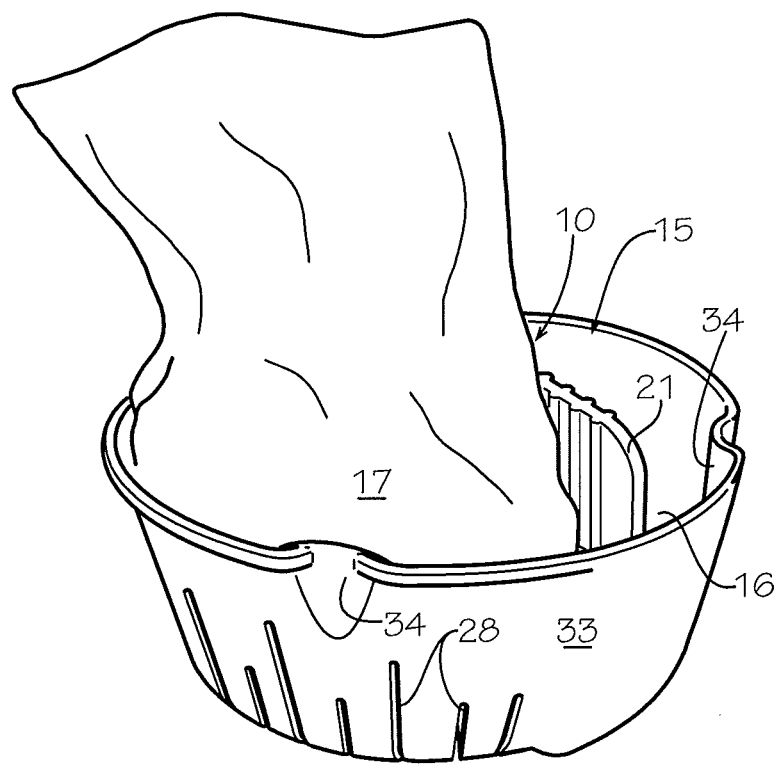
FIG. 5 is a perspective view of the basket with the granular moisture absorber in a transparent, liquid impervious bag for shipment to the end user.
Figure 6:
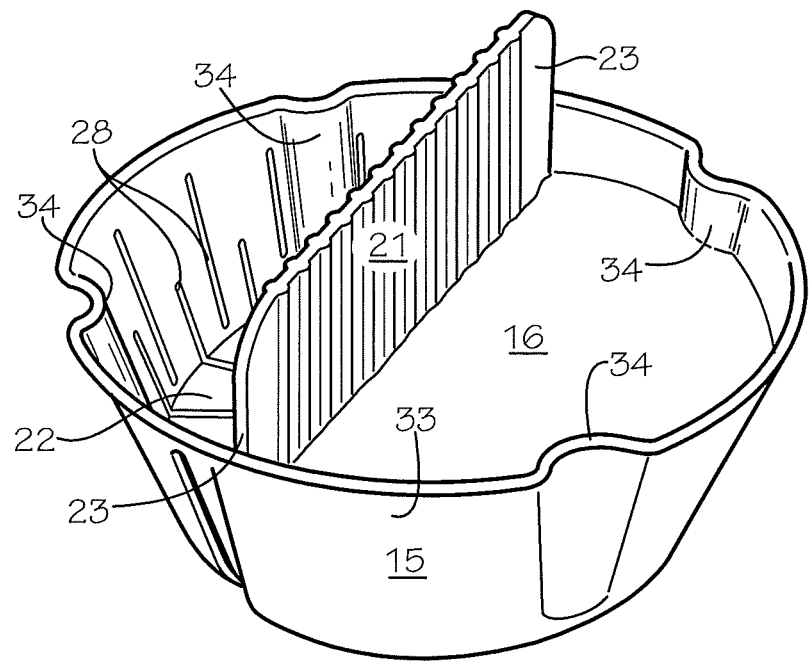
FIG. 6 is a perspective view of the basket with the solid air freshener and odor absorber placed in the basket.
Figure 7:
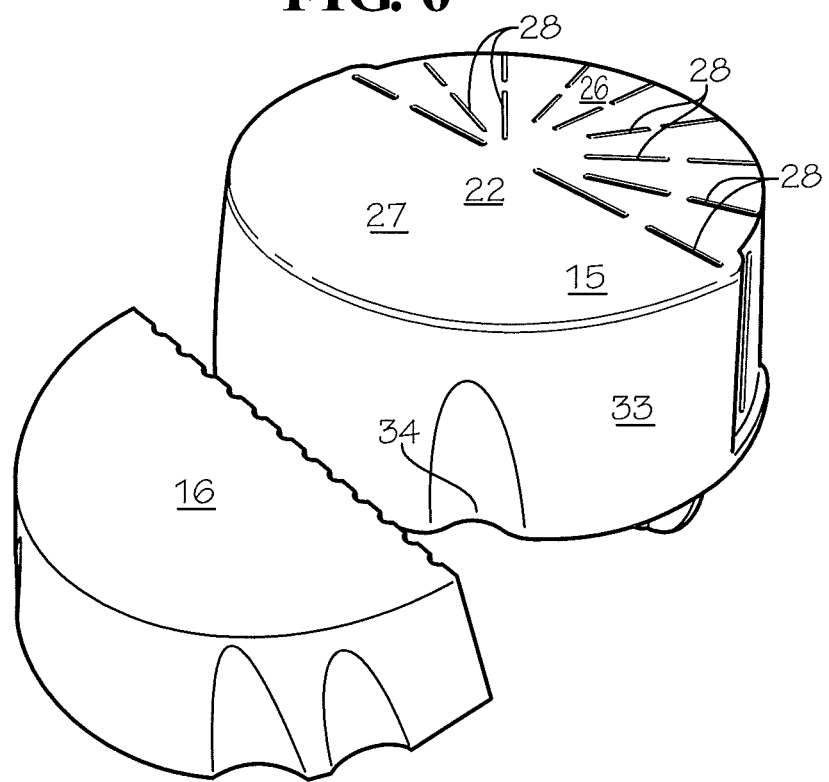
FIG. 7 is a perspective view of the basket when the basket is inverted, and also of the solid air freshener and odor absorber positioned adjacent the basket.
Figure 8:
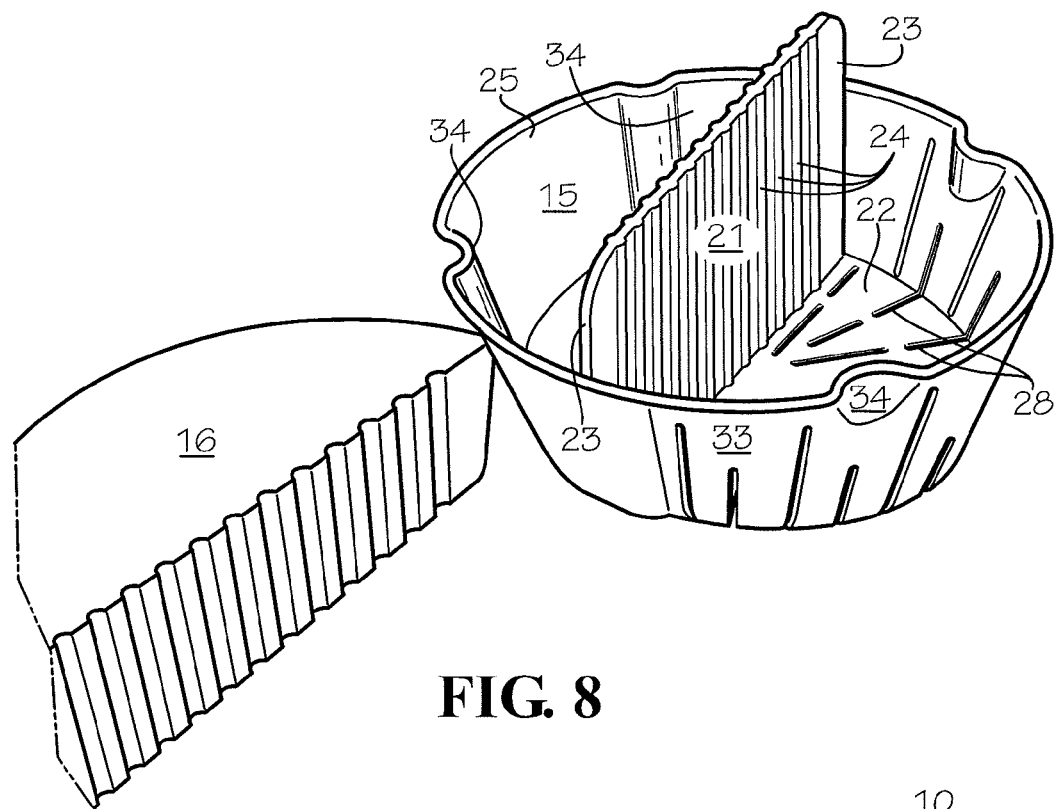
FIG. 8 is a perspective view of the basket and the solid air freshener and odor absorber positioned adjacent the basket.
Figure 9:
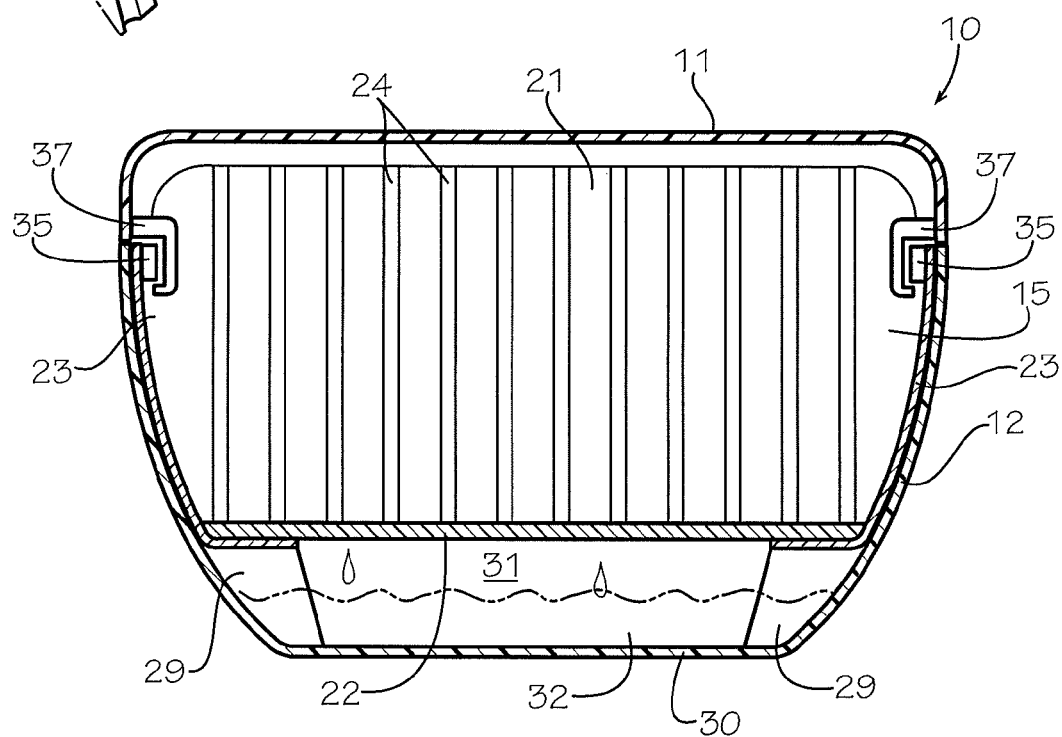
FIG. 9 is a side cross sectional view of the assembled product.

FIG. 4 illustrates the interior of the tub 12. The tub includes interior basket supports 29 that are spaced about the lower inner circular surface of the tub at positions that form basket supports for the bottom of the basket 15. As shown in FIGS. 4 and 9, the interior basket supports 29 are in the form of fins, and when the basket 15 is placed in the tub 12 the bottom wall 22 of the basket 15 rests on the interior basket supports and the bottom wall of the basket forms a false bottom over the bottom wall 30 of the tub 12. As shown in FIG. 9 the space between the false bottom 22 and the bottom wall 30 of the tub 12 is positioned so as to function as a moisture collection space 31 to receive the moisture 32 that is emitted by the granules of the moisture absorbent 17.

As shown in FIGS. 3 and 5-8, the annular side wall 33 of basket 15 at the rim of the basket defines four protruding folds 34 that extend inwardly from the perimeter of the rim of the basket and are spaced at intervals about the basket. As shown in FIG. 4, the tub 12 includes inwardly extending lock tabs 35 spaced at the same intervals about the upper interior of the tub 12. When the basket 15 is moved down into the tub 12 with the inwardly protruding folds 34 in registration with the lock tabs 35, the inwardly protruding folds pass the lock tabs and allow the basket to be fully moved into the tub until the lower portion of the basket rests on the interior basket supports 29. The vertical dimension of the basket when resting on the interior basket supports 29 is less than the distance between the interior basket supports 29 and the lock tabs 35 so upper rim 25 of the basket 15 is positioned at a lower level than the lock tabs 35. Once the basket has been positioned in the tub 12, the basket may be rotated by turning the vertical divider 21 so that the four inwardly protruding folds of the basket no longer register with the lock tabs 35 of the tub and the rim of the basket moves beneath the lock tabs and the basket cannot move vertically out of the tub. In this way, the lock tabs lock the basket in the interior of the tub so that if the product is inadvertently inverted, the basket 15 will not fall out of the tub 12. This is known as a "bayonet" coupling.

As shown in FIG. 9, a plurality of keepers 37 extend inwardly from the edge of the lid 11 and are spaced at intervals about the lid for locking engagement with lock tabs 35 of the tub 12. When the lid is rotated on the upper rim of the tub, the keepers engage the lock tabs and lock the lid to the tub.

From the foregoing, it should be understood that the product combines two items that function in one container, in that the granular moisture absorber 17 tends to collect and absorb moisture which may be expelled by the influence of gravity downwardly through the openings 28 in the bottom wall of the basket and accumulated in the collection space 31 beneath the bottom wall 30 of the tub 12. Also, the solid air freshener and odor absorber 16 in the other half of the basket tends to emit a fragrance for deodorizing and freshening the air about the product.

The vertical divider 21 facilitates the rotary movement and lifting of the basket 15 from the tub 12 so that the user of the product can open the lid 11 away from the tub 12 and lift the basket 15 and its contents from the tub 12 and pour the liquid collected in the tub out of the tub and then reinsert the basket and its contents back into the tub, all without releasing the tub and basket, in one action.

Further, the vertical divider 21 functions as a handle for the basket and the vertical ribs 24 of the vertical divider tend to strengthen the vertical divider and to guide the moisture emitted from the granules of the moisture absorbent, and move under the influence of gravity to the open slots 28 of the basket, to pass through the open slots 28 of the basket into the collection space 31 (FIG. 9).

It will be understood by those skilled in the art that while the foregoing description sets forth in detail preferred embodiments of the present invention, modifications, additions, and changes might be made thereto without departing from the spirit and scope of the invention.

The invention claimed is:

1. A multiple purpose container for air freshener, odor absorber and moisture absorber in a single product, comprising:
  a tub including a tub bottom wall and a side wall extending upwardly from said tub bottom wall and forming a rim displaced from said tub bottom wall,
  a lid applied to said rim, said lid defining air openings there through,
  a basket including a basket bottom wall, a basket sidewall extending upwardly about said basket bottom wall, and a vertical divider extending upwardly from said basket bottom wall and to said basket side wall and forming chambers in said basket on opposite sides of the vertical divider,
  said basket defining drain openings through one side of said vertical divider,
  said basket being impervious on the side of said basket opposite said one side of the vertical divider for supporting a solid odor absorber material that takes the shape of the second one of the chambers, and
  interior basket supports positioned upwardly from said tub bottom wall for supporting said basket bottom wall above said tub bottom wall and forming a liquid collection space between the tub bottom wall and the basket bottom wall.

2. The multiple purpose container of claim 1, and further including a label releasably adhered to said lid over said air openings.

3. The multiple purpose container of claim 1, wherein the lid includes a central portion spaced above the tub, the vertical divider of the basket extends upwardly higher than the rim of the tub and into space above the tub and the lid and is shaped to form a handle for lifting the basket out of the container to allow the container to be tilted to pour accumulated water out of the tub without the accumulated water contacting the air freshener in the basket.

4. The multiple purpose container of claim 1, wherein the vertical divider is formed with ribs that extend above the basket side wall.

5. The multiple purpose container of claim 1, wherein said tub and said basket form a bayonet connection for holding the basket in the tub.

6. A multiple purpose container for supporting a moisture absorber separately from other contents, comprising
  a basket including a basket bottom wall, a basket sidewall extending upwardly about said basket bottom wall, and a vertical divider extending upwardly from said basket bottom wall and to said basket side wall,
  said vertical divider forming chambers in said basket on opposite sides of the vertical divider, the bottom wall of the basket defining drain openings there through on one side of said vertical divider and the bottom wall on the other side of the vertical divider being impervious,
  a tub including a tub bottom wall and a side wall extending upwardly from said tub bottom wall and forming a rim displaced from said tub bottom wall, the tub being of a width and depth greater than the basket for receiving the basket,
  a lid applied to said rim, said lid defining air openings there through, the tub including interior basket supports positioned for supporting said basket bottom wall above said tub bottom wall and forming a liquid collection space between the tub bottom wall and the basket bottom wall.

7. The multiple purpose container of claim 6, and further including a moisture absorber positioned in said basket on one side of said vertical divider at said drain openings, and an odor absorber positioned in said basket on the other side of said vertical divider.

* * * * *